US009469576B2

(12) United States Patent
Butler

(10) Patent No.: US 9,469,576 B2
(45) Date of Patent: *Oct. 18, 2016

(54) ALKYLATION OF BENZENE WITH A HYDROCARBON GAS

(71) Applicant: FINA TECHNOLOGY, INC., Houston, TX (US)

(72) Inventor: James R. Butler, Spicewood, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/252,219

(22) Filed: Apr. 14, 2014

(65) Prior Publication Data

US 2014/0221717 A1    Aug. 7, 2014

Related U.S. Application Data

(60) Division of application No. 13/178,091, filed on Jul. 7, 2011, now Pat. No. 8,742,190, which is a continuation-in-part of application No. 13/024,602, filed on Feb. 10, 2011, now Pat. No. 8,426,661, which is a continuation of application No. 11/650,282, filed on Jan. 5, 2007, now abandoned.

(60) Provisional application No. 60/756,778, filed on Jan. 7, 2006.

(51) Int. Cl.
*C07C 2/66* (2006.01)

(52) U.S. Cl.
CPC ............. *C07C 2/66* (2013.01); *C07C 2523/10* (2013.01); *C07C 2529/06* (2013.01); *C07C 2529/08* (2013.01); *C07C 2529/70* (2013.01)

(58) Field of Classification Search
CPC ............ C07C 2/66; B01J 38/04; B01J 38/02
USPC ...................... 585/467; 502/34, 56
See application file for complete search history.

(56) References Cited

U.S. PATENT DOCUMENTS

| 3,308,069 A | 3/1967 | Wadlinger et al. |
| 4,185,040 A | 1/1980 | Ward et al. |
| 4,642,226 A | 2/1987 | Calvert et al. |
| 4,891,458 A * | 1/1990 | Innes ................... B01J 29/7007 585/323 |
| 5,082,990 A * | 1/1992 | Hsieh ................... C10G 29/205 208/46 |
| 5,959,168 A * | 9/1999 | van der Aalst ........... C07C 2/66 585/313 |
| 6,252,126 B1 * | 6/2001 | Netzer ................... B01D 3/009 422/623 |

* cited by examiner

*Primary Examiner* — Thuan D Dang
(74) *Attorney, Agent, or Firm* — Albert Shung

(57) ABSTRACT

Methods of forming ethylbenzene are described herein. In one embodiment, the method includes contacting dilute ethylene with benzene in the presence of an alkylation catalyst to form ethylbenzene, wherein such contact occurs in a reaction zone containing a gaseous phase and recovering ethylbenzene from the reaction zone.

3 Claims, 5 Drawing Sheets

Temperature Versus Age
Bed 1

Temperature Versus Age
Bed 2

Byproducts Versus Age

ALKYLATION OF BENZENE WITH A HYDROCARBON GAS

CROSS-REFERENCE TO RELATED APPLICATIONS

This application is a divisional of U.S. application Ser. No. 13/178,091, filed Jul. 7, 2011, which is a continuation-in-part (CIP) of U.S. application Ser. No. 13/024,602, filed Feb. 10, 2011, now issued as U.S. Pat. No. 8,426,661, which is a continuation of U.S. application Ser. No. 11/650,282, filed Jan. 5, 2007, now abandoned, which claims the benefit of U.S. Provisional Patent Application Ser. No. 60/756,778, filed Jan. 7, 2006, now expired.

FIELD

Embodiments of the present invention generally relate to alkylation of benzene to ethylbenzene. In particular, embodiments of the present invention relate to alkylation of benzene with a dilute ethylene stream.

BACKGROUND

As a result of the high cost of pure (or high purity) ethylene, efforts have been directed to utilizing dilute ethylene in the alkylation of benzene to form ethylbenzene.

While it has been discovered that the use of dilute ethylene generally results in low xylene formation, the high methane and hydrogen content thereof generally results in a bubble point temperature of the combined mixture of dilute ethylene and benzene that is very low. For example, the bubble point temperature may be lower than the activity temperature of the ethylation catalyst. Accordingly, it has not been possible for liquid phase alkylation of dilute ethylene.

A need exists to develop a method of utilizing lower cost ethylene in alkylation reactions.

SUMMARY

An embodiment, either by itself or in combination with other embodiments, is a method of forming ethylbenzene that includes contacting a first stream that includes ethylene with benzene in an alkylation reaction zone having a plurality of catalyst beds comprising an alkylation catalyst to form ethylbenzene. Ethylbenzene is recovered from the alkylation reaction zone. The first stream includes a gaseous phase and the weight ratio of benzene:first stream per catalyst bed is less than 28:1.

In an embodiment the alkylation catalyst can be cerium promoted and can include a zeolite beta. The weight ratio of benzene to first stream can range from 3:1 to 28:1 per catalyst bed. The alkylation catalyst can have a silica to alumina molar ratio of from about 10:1 to about 200:1. The reaction temperature can range from about 160° C. to about 270° C.

An embodiment, either by itself or in combination with other embodiments, is a method of forming ethylbenzene by contacting a dilute ethylene stream with benzene in a plurality of catalyst beds comprising cerium promoted zeolite alkylation catalyst to form ethylbenzene. The dilute ethylene stream is in the presence of the cerium promoted zeolite alkylation catalyst in a weight ratio of benzene:dilute ethylene less than 28:1 per catalyst bed and comprises ethylene in amounts ranging from 7 to 25 wt. % based on the total weight of the dilute ethylene stream.

The zeolite can be selected from beta and Y. The reaction temperature can range from about 160° C. to about 270° C. At least a portion of the dilute ethylene can be in a gaseous phase in the presence of the cerium promoted zeolite alkylation catalyst.

An embodiment, either by itself or in combination with other embodiments, is a method of introducing benzene to an alkylation reaction zone containing an alkylation catalyst, introducing an ethylene containing stream to the alkylation reaction zone, wherein the ethylene containing stream is introduced in a manner to contact the benzene and the alkylation catalyst in a plurality of catalyst beds, and recovering a product stream from the reaction zone that has 0.8 wt. % or less butylbenzene content. At least a portion of the ethylene containing stream is in a gaseous phase and the weight ratio of benzene:ethylene containing stream per catalyst bed is less than 28:1.

The alkylation catalyst can be a cerium promoted zeolite beta. The product stream can include 0.2 wt. % or less butylbenzene.

An embodiment, either by itself or in combination with other embodiments, is a method of forming ethylbenzene by contacting benzene with a hydrocarbon gas in a benzene:hydrocarbon gas weight ratio of about 28:1 or less per catalyst bed, wherein the contact occurs in a plurality of catalyst beds comprising an alkylation catalyst, and recovering ethylbenzene from the alkylation reaction zone.

The hydrocarbon gas can be present in a benzene:hydrocarbon gas weight ratio ranging from 2:1 to 28:1 per catalyst bed, optionally from 5:1 to 21:1 per catalyst bed. The alkylation catalyst can be a cerium promoted zeolite. At least a portion of the alkylation reaction zone can be operated in a gaseous phase. The hydrocarbon gas can include ethylene and another gas selected from the group consisting of methane, ethane, and combinations thereof.

The embodiments disclosed herein are usable and combinable with every other embodiment disclosed herein, and consequently, this disclosure is enabling for any and all combinations of the embodiments disclosed herein.

DETAILED DESCRIPTION

Introduction and Definitions

Figure 1A:
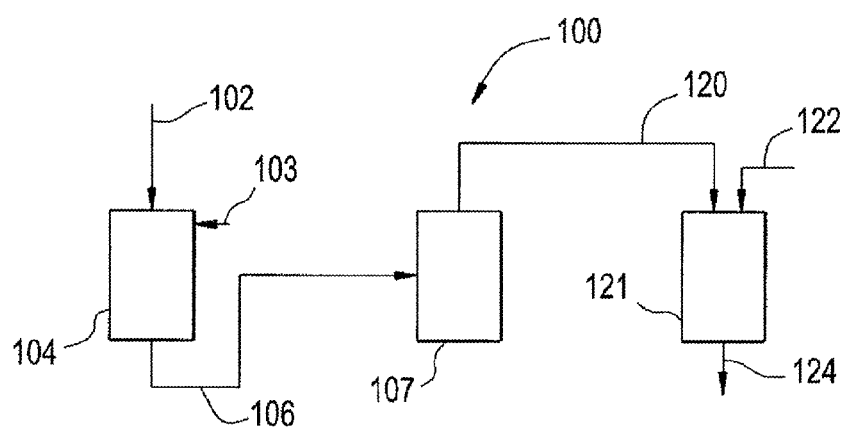
FIGS. 1A and 1B illustrate an embodiment of an alkylation/transalkylation process.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions when the information in this patent is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

The term "activity" refers to the weight of product produced per weight of the catalyst used in a process per hour of reaction at a standard set of conditions (e.g., grams product/gram catalyst/hr).

The term "alkyl" refers to an alkane absent hydrogen.

The term "alkylation" refers to the transfer of an alkyl group from one molecule to another.

The term "deactivated catalyst" refers to a catalyst that has lost enough catalyst activity to no longer be efficient in a specified process. Such efficiency is determined by individual process parameters.

The term "olefin" refers to a hydrocarbon with a carbon-carbon double bond.

The term "processing" is not limiting and includes agitating, mixing, milling, blending and combinations thereof, all of which are used interchangeably herein. Unless otherwise specified, the processing may occur in one or more vessels, such vessels being known to one skilled in the art.

The term "recycle" refers to returning an output of a system as input to either that same system or another system within a process. The output may be recycled to the system in any manner known to one skilled in the art, for example, by combining the output with an input stream or by directly feeding the output into the system. In addition, multiple input/recycle streams may be fed to a system in any manner known to one skilled in the art.

The term "regenerated catalyst" refers to a catalyst that has regained enough activity to be efficient in a specified process. Such efficiency is determined by individual process parameters.

The term "regeneration" refers to a process for renewing catalyst activity and/or making a catalyst reusable after its activity has reached an unacceptable/inefficient level. Examples of such regeneration may include passing steam over a catalyst bed or burning off carbon residue, for example.

FIG. 1A illustrates a schematic block diagram of an embodiment of an alkylation/transalkylation process 100. Although not shown herein, the process stream flow may be modified based on unit optimization so long as the modification complies with the spirit of the invention, as defined by the claims. For example, at least a portion of any overhead fraction may be recycled as input to any other system within the process and/or any process stream may be split into multiple process stream inputs, for example. Also, additional process equipment, such as heat exchangers, may be employed throughout the processes described herein and such placement is generally known to one skilled in the art. Further, while described below in terms of primary components, the streams indicated below may include any additional components as known to one skilled in the art.

The process 100 generally includes supplying an input stream 102 to an alkylation system 104. The alkylation system 104 is generally adapted to contact the input stream 102 with an alkylation catalyst to form an alkylation output stream 106. In addition to the input stream 102, an additional input, such as an alkylating agent, is generally supplied to the alkylation system 104 via line 103.

At least a portion of the alkylation output stream 106 passes to a separation system 107. The separation system 107 generally includes a plurality of vessels, such vessels being adapted to separate components of the output stream 106. At least a portion of the separation system output, described in further detail below, is passed from the separation system 107 to a second alkylation system (i.e., a transalkylation system 121) as transalkylation input 120.

In addition to the transalkylation input 120, an additional input, such as additional aromatic compound, is generally supplied to the transalkylation system 121 via line 122 to contact a transalkyation catalyst and form a transalkylation output 124.

The input stream 102 generally includes a first aromatic compound. The aromatic compound may include substituted or unsubstituted aromatic compounds. In a specific embodiment, the first aromatic compound includes benzene. The benzene may be supplied from a variety of sources, such as a fresh benzene source and/or a variety of recycle sources. As used herein, the term "fresh benzene source" refers to a source including at least about 95 wt. % benzene, at least about 98 wt. % benzene or at least about 99 wt. % benzene, for example. As used herein, the term "recycle" refers to an output of a system, such as an alkylation system and/or a dehydrogenation system, which is then returned as input to either that same system or another system the same process.

The alkylating agent 103 generally includes ethylene. In a specific embodiment, the alkylating agent includes dilute ethylene. As used herein, the term "dilute ethylene" refers to alkylating agent streams having less than about 50 wt. % ethylene. For example, the alkylating agent may include from about 1 to about 50 wt. %, optionally from about 7 to about 25 wt. % or from about 10 to about 15 wt. % ethylene. The dilute ethylene stream may further include methane, hydrogen or ethane, for example.

The dilute ethylene stream may be present in any desired amounts in the alkylation reaction zone. Benzene:dilute ethylene stream ratios are provided using the ranges for percent ethylene present in the dilute ethylene stream provided herein and the benzene:ethylene ratios provided herein. Specifically, dilute ethylene streams having less than 50 wt. % ethylene, 1-50 wt. % ethylene, 7-25 wt. % ethylene, and 10-15 wt. % ethylene, were each applied to the benzene:ethylene molar ratios of 20:1, 18:1, 15:1, 10:1, 8:1, and 6:1. The molar ratio of benzene to ethylene of 1:1 equates to a benzene:ethylene weight ratio of 2.8:1, due to benzene having a molar mass of about 2.8 times the molar mass of ethylene. The benzene portion of the benzene:ethylene ratio was multiplied by the percent ethylene in each dilute ethylene stream embodiment and by 2.8, resulting in benzene:dilute ethylene weight ratios. In an embodiment, the benzene:dilute ethylene weight ratio in each catalyst bed is about 28:1 or less, optionally from 25:1 or less, optionally from 21:1 or less, optionally from 14:1 or less, optionally from 11:1 or less, or optionally from 8.5:1 or less.

In another embodiment, the dilute ethylene stream is present in the alkylation reaction zone in a benzene:dilute ethylene weight ratio in each catalyst bed of from 0.28:1 to 28:1, optionally from 1:1 to 25:1, or optionally from 5:1 to 21:1. In yet another embodiment, the benzene:dilute ethylene weight ratio in each catalyst bed can range from 3:1 to 28:1. A benzene:dilute ethylene stream weight ratio of 3:1 equates to a benzene:ethylene molar ratio of 15:1 at a dilute ethylene of 7 wt % ethylene. A benzene:dilute ethylene stream weight ratio of 28:1 equates to a benzene:ethylene molar ratio of 20:1 at a dilute ethylene of 50 wt % ethylene.

The alkylation of benzene with ethylene is known to be successful in liquid phase reactions utilizing a cerium promoted zeolite catalyst and a benzene:ethylene molar ratio from 15:1 to 20:1 without significant catalyst deactivation. At these benzene:ethylene molar ratios the ethylene is substantially entirely dissolved within the benzene liquid phase. It has been found that utilizing a dilute ethylene alkylating stream the entire dilute ethylene stream does not have to be dissolved within the benzene stream, and the alkylation of benzene with ethylene can be successful in two phase reactions utilizing a cerium promoted zeolite catalyst without significant catalyst deactivation.

Dilute ethylene may be supplied from any source known to one skilled in the art. For example, the dilute ethylene may be produced from fluid catalytic cracking (FCC).

In addition to the first aromatic compound and the alkylating agent, the input stream 102 may further include other compounds in minor amounts (e.g., sometimes referred to as poisons or inactive compounds,) such as toluene, ethyl benzene, $C_7$ aliphatic compounds and/or nonaromatic compounds, for example. In one embodiment, the input stream 102 includes less than about 3 wt. % of such compounds or less than about 1 wt. %, for example.

The alkylation reaction zone may be operated under a two-phase reaction. In the two-phase alkylation reaction, at least a portion of the alkylating agent may be present in the gaseous phase. In an embodiment, the alkylating agent may be present in the alkylation reaction zone in both the gaseous phase and the liquid phase. In an embodiment, the alkylation reaction zone may be operated under conditions at which at least a portion of the alkylating agent is in the gaseous phase and the entirety of the aromatic compound is in the liquid phase, for example the benzene can be in the liquid phase while a dilute ethylene stream can be in both a gaseous and liquid phase.

In an embodiment, the total gas in the alkylation reaction zone may be present in any desired amounts relative to the total amount of aromatic compound(s) present in the alkylation reaction zone. The ratios of benzene:total gas were obtained in the same manner as the ratios of benzene:dilute ethylene stream as provided herein. In an embodiment, the total gas is present in the alkylation reaction zone in a benzene:total gas weight ratio in each catalyst bed of about 28:1 or less, or about 25:1 or less, or about 21:1 or less. In another embodiment, the total gas is present in the alkylation reaction zone in a benzene:total gas weight ratio in each catalyst bed of from 0.28:1 to 28:1, optionally from 1:1 to 25:1, or optionally from 5:1 to 21:1. The total gas in the alkylation reaction zone may include any component capable of being in a gaseous phase under the alkylation reaction conditions disclosed herein. In an embodiment, the total gas in the alkylation reaction zone may include any combination of methane, ethane, ethylene and hydrogen, and optionally $CO_2$. In another embodiment, the total gas in the alkylation reaction zone may include any combination of methane, ethane, ethylene, hydrogen, oxygen, $CO_2$, and nitrogen.

The alkylation reaction zone can include any variation of types and amounts of hydrocarbon gases. In an embodiment, the total hydrocarbon gas present in the alkylation reaction zone during alkylation includes methane, ethane and ethylene. In another embodiment, the total hydrocarbon gas includes ethylene and another gas selected from the group consisting of methane, ethane, and combinations thereof. In an embodiment, the total hydrocarbon gas in the alkylation reaction zone may be present in any desired amounts relative to the total amount of aromatic compound(s) present in the alkylation reaction zone. The ratios of benzene:total hydrocarbon gas were obtained in the same manner as the ratios of benzene:dilute ethylene as provided herein. In an embodiment, the weight ratio of benzene:total hydrocarbon gas in each catalyst bed ranges from about 28:1 or less, or about 25:1 or less or about 21:1 or less. In another embodiment, the total hydrocarbon gas is present in the alkylation reaction zone in a benzene:total hydrocarbon gas weight ratio in each catalyst bed of from 0.28:1 to 28:1, optionally from 1:1 to 25:1, or optionally from 5:1 to 21:1.

The alkylation system 104 generally includes one or more reaction vessels. The reaction vessels may include continuous flow reactors (e.g., fixed-bed, slurry bed or fluidized bed,) for example. In one embodiment, the alkylation system 104 includes a plurality of multi-stage reaction vessels (not shown). For example, the plurality of multi-stage reaction vessels may include a plurality of operably connected catalyst beds, such beds containing an alkylation catalyst (not shown.) The number of catalyst beds is generally determined by individual process parameters, but may include from 2 to 20 catalyst beds or from 3 to 10 catalyst beds, for example.

In an embodiment, such reaction vessels may be liquid phase reactors operated at reactor temperatures and pressures sufficient to maintain the alkylation reaction in the corresponding phase, i.e., the phase of the aromatic compound, for example. In one embodiment, the plurality of stages within a reaction vessel may be operated with the same or different catalyst and at the same or different temperatures and space velocities. Such temperatures and pressures are generally determined by individual process parameters. However, liquid phase reactions may occur at temperatures of from about 160° C. to about 270° C. at 600 psig.

The alkylation catalyst generally includes a cerium promoted molecular sieve catalyst. In one embodiment, the cerium promoted catalyst is a cerium promoted zeolite beta catalyst. The cerium promoted zeolite (e.g., cerium beta) catalyst may be formed from any zeolite catalyst known to one skilled in the art. For example, the cerium beta catalyst may include zeolite beta modified by the inclusion of cerium. Any method of modifying the zeolite beta catalyst with cerium may be used.

The zeolite beta may have a silica to alumina molar ratio (expressed as $SiO_2/Al_2O_3$) of from about 10 to about 200 or about 20 to about 150, for example. In one embodiment, the zeolite beta may have a low sodium content, e.g., less than about 0.2 wt. % expressed as $Na_2O$, or less than about 0.02 wt. %, for example. The sodium content may be reduced by any method known to one skilled in the art, such as through ion exchange, for example. The formation of zeolite beta is further described in U.S. Pat. Nos. 3,308,069 and 4,642,226, which are incorporated by reference herein.

In another embodiment, it is contemplated that a cerium promoted zeolite Y catalyst may be used. It is further contemplated that the zeolite Y catalyst may be modified with cerium in the same manner as the modification of zeolite beta. The formation of Zeolite Y is described in U.S. Pat. No. 4,185,040, which is incorporated by reference herein.

The alkylation catalyst may optionally be bound to, supported on or extruded with any support material. For example, the alkylation catalyst may be bound to a support to increase the catalyst strength and attrition resistance. The support material may include alumina, silica, aluminosilicate, titanium and/or clay, for example.

The alkylation catalyst can continue with alkylation at benzene:ethylene molar ratios of 20:1 or less, optionally 18:1 or less, optionally 15:1 or less, optionally 10:1 to 3:1, optionally 8:1 to 5:1, and optionally about 6:1 for at least 10 days, optionally at least 20 days, optionally at least 30 days, and optionally at least 40 days, without significant deactivation. In an embodiment, the alkylation catalyst can continue under alkylation conditions at benzene:ethylene molar ratios of 15:1 or less, optionally 10:1 to 3:1, optionally 8:1 to 5:1, and optionally about 6:1, under temperatures of at least 200° C. with a temperature increase ranging from 1.0-0.01° C./day, optionally 0.1-0.01° C./day, and optionally 0.05-0.01° C./day, for at least 10 consecutive days on stream, optionally at least 20 consecutive days on stream, and optionally at least 30 consecutive days on stream.

The alkylation output 106 generally includes a second aromatic compound formed from the reaction of the first aromatic compound and the alkylating agent in the presence of the alkylation catalyst, for example. In a specific embodiment, the alkylation output 106 includes ethylbenzene. The alkylation output 106 further includes less than about 1 wt. %, or less than about 0.8 wt. % or less than about 0.2 wt. % butylbenzenes, such as sec-butylbenzene, for example.

The transalkylation system 120 generally includes one or more reaction vessels having a transalkylation catalyst disposed therein. The reaction vessels may include any reaction vessel, combination of reaction vessels and/or number of reaction vessels (either in parallel or in series) known to one skilled in the art. Such temperatures and pressures are generally determined by individual process parameters. However, liquid phase reactions may occur at temperatures of from about 65° C. to about 290° C. (e.g., the critical temperature of the first aromatic compound) and pressures of from about 600 psig or less, for example. Vapor phase reactions may occur at temperatures of from about 420° C. to about 450° C., for example.

The transalkylation output 124 generally includes the second aromatic compound, for example. As stated previously, any of the process streams, such as the transalkylation output 124, may be used for any suitable purpose or recycled back as input to another portion of the system 100, such as the separation system 107, for example.

The transalkylation catalyst may include a molecular sieve catalyst and may be the same catalyst or a different catalyst than the alkylation catalyst, for example. Such molecular sieve catalyst may include zeolite beta, zeolite Y, zeolite MCM-22, zeolite MCM-36, zeolite MCM-49 or zeolite MCM-56, for example.

In a specific embodiment, the first aromatic compound includes benzene and the alkylating agent includes dilute ethylene. In one embodiment, the molar ratio of benzene to ethylene in the input stream 102 may be about 10:1 or less, or about 8:1 or less or about 6:1 or less in each catalyst bed and the space velocity may be from about 2 to about 100, for example. In an embodiment, the molar ratio of benzene to ethylene in the input stream 102 may be about 20:1 or less in each catalyst bed, or about 18:1 or less in each catalyst bed, or may range from about 10:1 to 20:1 in each catalyst bed. In a further embodiment, the molar ratio may be from about 5.5:1 to 8:1 in each catalyst bed. The molar ratio of benzene to ethylene of 1:1 equates to a benzene:ethylene weight ratio of 2.8:1, due to benzene having a molar mass of about 2.8 times the molar mass of ethylene.

In a specific embodiment, benzene is recovered through line 110 and recycled (not shown) as input to the alkylation system 104, while ethylbenzene and/or polyalkylated benzenes are recovered via lines 116 and 120 respectively.

Figure 1B:
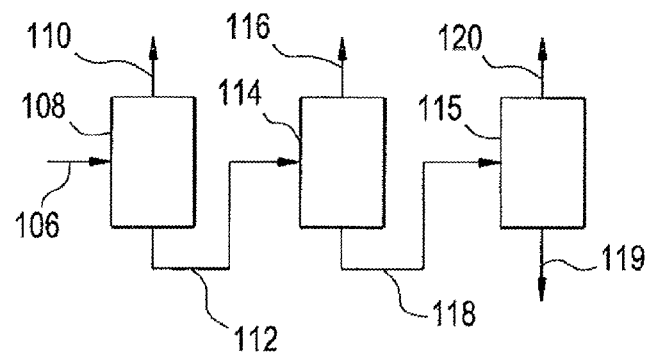

In a specific embodiment, the separation system (or product recovery) 107 includes three separation zones (illustrated in FIG. 1B) operated at conditions known to one skilled in the art. The first separation zone 108 may include any process or combination of processes known to one skilled in the art for the separation of aromatic compounds. For example, the first separation zone 108 may include one or more distillation columns (not shown,) either in series or in parallel. The number of such columns may depend on the volume of the alkylation output 106 passing therethrough, for example. While the temperature and pressure are system specific, the first separation zone temperature may be from about 130° C. to about 170° C. and the pressure may be atmospheric pressure to 50 psig, for example.

The overhead fraction 110 from the first column 108 generally includes the first aromatic compound, such as benzene, for example.

The bottoms fraction 112 from the first separation zone 108 generally includes the second aromatic compound, such as ethylbenzene, for example. The bottoms fraction 112 further includes additional components, which may undergo further separation in the second separation zone 114 and third separation zone 115, discussed further below.

The second separation zone 114 may include any process known to one skilled in the art, for example, one or more distillation columns (not shown), either in series or in parallel. While the temperature and pressure are system specific, the first separation zone temperature may be from about 180° C. to about 240° C. and the pressure may be from about 100 psig to about 500 psig, for example.

The overhead fraction 116 from the second separation zone 114 generally includes the second aromatic compound, such as ethylbenzene, which may be recovered and used for any suitable purpose, such as the production of styrene, for example.

The bottoms fraction 118 from the second separation zone 114 generally includes heavier aromatic compounds, such as polyethylbenzene, cumene and/or butylbenzene, for example, which may undergo further separation in the third separation zone 115.

The third separation zone 115 generally includes any process known to one skilled in the art, for example, one or more distillation columns (not shown), either in series or in parallel. While the temperature and pressure are system specific, the first separation zone temperature may be from about 180° C. to about 240° C. and the pressure may be atmospheric pressure to about 50 psig, for example.

In a specific embodiment, the overhead fraction 120 from the third separation zone 115 may include diethylbenzene and liquid phase triethylbenzene, for example. The bottoms fraction 119 (e.g., heavies) may be recovered from the third separation zone 115 for further processing and recovery (not shown).

Unfortunately, alkylation and transalkylation catalysts generally experience deactivation upon exposure to reaction. The life of the catalyst generally depends on process conditions and catalyst type. However, when regeneration of any catalyst within the system is desired, the regeneration procedure generally includes processing the deactivated catalyst at high temperatures, although the regeneration may include any regeneration procedure known to one skilled in the art.

Once a reactor is taken off-line, the catalyst disposed therein may be purged. Off-stream reactor purging may be performed by contacting the catalyst in the off-line reactor with a purging stream, which may include any suitable inert gas (e.g., nitrogen), for example. The off-stream reactor purging conditions are generally determined by individual process parameters and are generally known to one skilled in the art.

The catalyst may then undergo regeneration. The regeneration conditions may be any conditions that are effective for at least partially reactivating the catalyst and are generally known to one skilled in the art. For example, regeneration may include heating the catalyst to a temperature or a series of temperatures, such as a regeneration temperature of from about 50° C. to about 200° C. above the purging or reaction temperature, for example.

In one embodiment, the catalyst is heated to a first temperature (e.g., 700° F.) for a time sufficient to provide an output stream having an oxygen content of about 0.5%. The catalyst may then be heated to a second temperature for a time sufficient to provide an output stream having an oxygen content of about 2.0%. The second temperature may be about 50° F. greater than the first temperature, for example. The second temperature is generally about 950° F. or less, for example. The catalyst may further be held at the second temperature for a period of time, or at a third temperature that is greater than the second temperature, for example.

Upon catalyst regeneration, the catalyst may then be reused for alkylation and transalkylation, for example.

Unexpectedly, no increase in the butylbenzene yield was observed.

EXAMPLES

In this example, an alkylation reaction of benzene with ethylene over a cerium promoted zeolite was run for over 200 days. The catalyst was a cerium promoted zeolite beta produced by Sud Chemie. The Sud Chemie Ce Beta zeolite was tested for liquid phase alkylation.

Ethylene solubility has typically been a problem at low benzene:ethylene ratios. According to the thermodynamics, not all the ethylene will typically dissolve with a molar ratio less than 15 under the reaction conditions. The benzene:ethylene ratio was initially adjusted to a molar ratio of 17:1 at the first catalyst bed to ensure that all of the ethylene would be dissolved in the liquid benzene before contact with the first catalyst bed. Initially, a recycle of the reactor effluent was used to keep a high hydrocarbon ethylene ratio to ensure solubility of all the ethylene. However, this caused excessive diethylbenzene (DEB) yields, contributing to more than expected residue yields. After the recycle was stopped, the residue yields were less than 0.5%.

The alkylation experiment used two catalyst beds in series. Some of the test data is shown in the Table below:

TABLE 1

Experimental Test Data

| | |
|---|---|
| Fresh Benzene Feed | 2.60 g/min |
| Recycle Rate | 10.40 g/min |
| Reactor 1 Ethylene Rate | 0.259 g/min |
| Reactor 2 Ethylene Rate | 0.259 g/min |
| Reactor 1 Bed Volume | 48 ml |
| Reactor 2 Bed Volume | 48 ml |
| Pressure | 500 psig |
| Temperature | 200° C. for both reactors |
| LSHV per reactor | 8.5 hr$^{-1}$ |

The molar ratio of benzene:ethylene at 17:1 is the predicted minimum ratio to maintain ethylene in a dissolved state. After the benzene recycle was stopped, the ethylene ratio was slowly dropped to a 5:1 molar ratio of benzene:ethylene. At the 5:1 ratio, the reactor was hard to control because the exotherm was large enough to start vaporizing some of the benzene or causing the reaction mixture to cross into the super critical state. In addition, the pressure was not controllable at these conditions. At a 6:1 molar ratio of benzene:ethylene, the unit was stable without adverse effects on the by-products.

Figure 2:
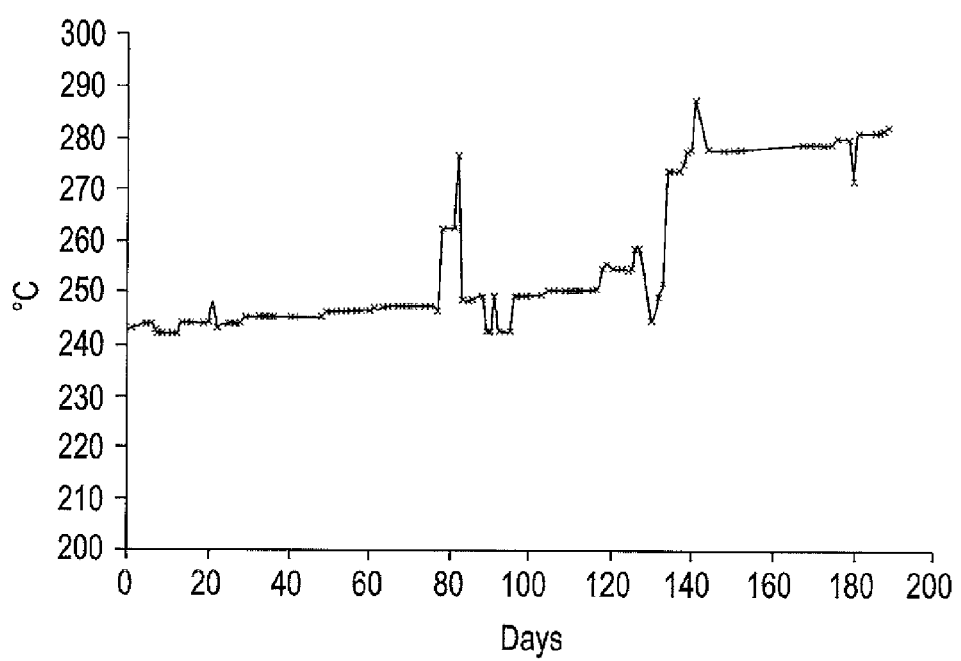
FIG. 2 is a graph showing catalyst temperature versus catalyst age on stream for bed 1 of the alkylation run in the Example.
Figure 3:
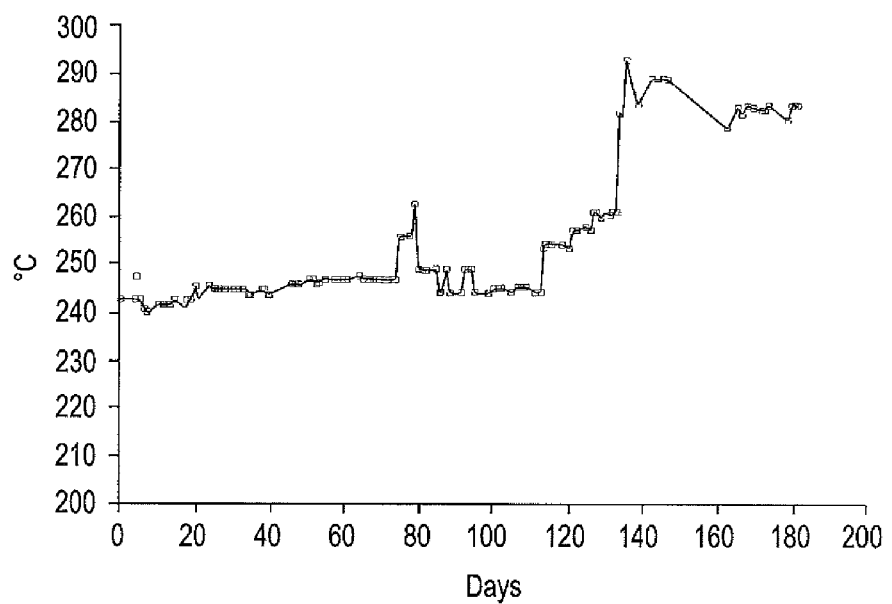
FIG. 3 is a graph showing catalyst temperature versus catalyst age on stream for bed 2 of the alkylation run in the Example.
Figure 4:
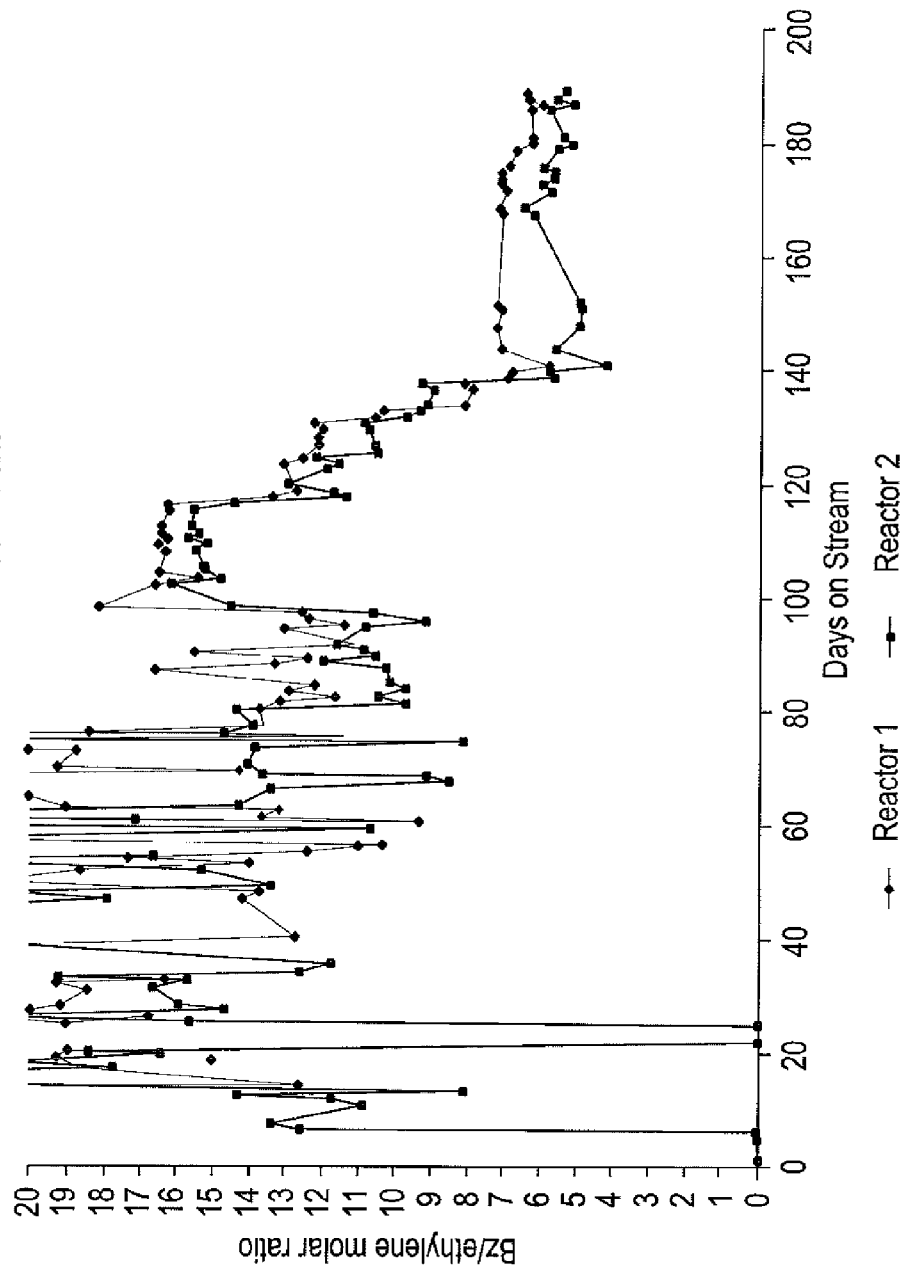
FIG. 4 is a graph showing the benzene:ethylene ratio versus catalyst age on stream for beds 1 and 2 of the alkylation run in the Example.

The temperature graph of FIG. 2 shows the amount of deactivation of the first reactor bed. After about day 140, the feed to the first reactor was changed to a 6:1 molar ratio of benzene:ethylene. FIG. 4 shows a transition to a 6:1 molar ratio of benzene:ethylene at about day 144, which was maintained until about day 180. During the 6:1 ratio run, as seen in FIG. 2, a stable temperature profile was observed in the first reactor bed with only a slight yet steady increase in temperature. Catalyst deactivation is made apparent by an increase in catalyst bed temperature, however this slight increase in temperature shown in FIG. 2 was likely due to the removal of impurities in the feed stream(s) and not catalyst deactivation since, as seen in FIG. 3, the second reactor bed showed no such increase in temperature.

Data from FIG. 2 is shown in Table 2.

TABLE 2

Reactor Bed 1 Temperature Data

| Days | T (° C.) |
|---|---|
| 140 | 287 |
| 150 | 278 |
| 160 | 278 |
| 170 | 279 |
| 180 | 280 |
| 190 | 280 |

The temperature graph of FIG. 3 demonstrates a steady temperature profile in the second reactor bed once the benzene:ethylene molar ratio was lowered to about 6:1. The temperature profile shows no overall increase in temperature from about day 150 to about day 190. No temperature increase in the reactor bed corresponds to no deactivation of the catalyst bed. Thus, no catalyst deactivation was observed in the second catalyst bed for that time period in which, according to FIG. 4, the benzene:ethylene molar ratio was about 6:1. Data from FIG. 3 is shown in Table 3.

TABLE 3

Reactor Bed 2 Temperature Data

| Days | T (° C.) |
|---|---|
| 140 | 295 |
| 150 | 290 |
| 160 | 281 |
| 170 | 280 |
| 180 | 282 |
| 190 | 282 |

Figure 5:
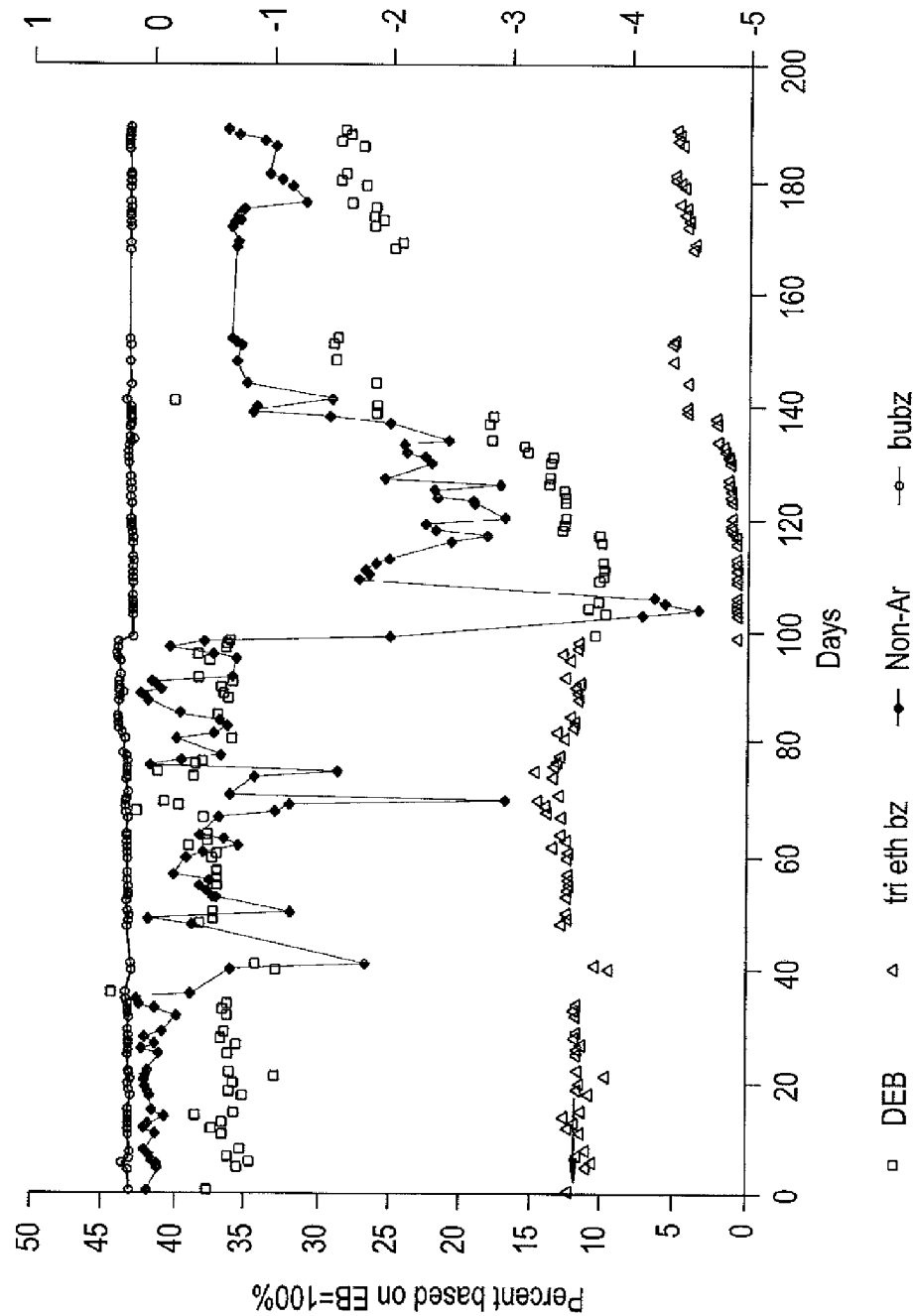
FIG. 5 is a graph showing percent byproducts versus catalyst age on stream for the alkylation run in the Example.

Also, as demonstrated by FIG. 5, a benzene:ethylene molar ratio of 6:1 causes no substantial increase in unwanted by-products. According to FIG. 5, after about day 150 when the benzene:ethylene molar ratio is about 6:1, the butylbezene production remains unchanged. FIG. 5 shows that the level of non-aromatics drops at a 6:1 benzene:ethylene ratio when compared to the level of non-aromatics at a 17:1 ratio during the first 100 days on stream (see also FIG. 4). FIG. 5 also shows that the level of triethyl-benzene drops at a 6:1 benzene:ethylene ratio when compared to the level of triethyl-benzene at a 17:1 ratio during the first 100 days on stream (see also FIG. 4). Also, FIG. 5 shows that the level of diethyl-benzene remains constant or drops slightly at a 6:1 benzene:ethylene ratio when compared to the level of diethyl-benzene at a 17:1 ratio during the first 100 days on stream (see also FIG. 4). The negative values for non-aromatics indicates some conversion over the alkylation catalyst.

TABLE 4

Reaction Byproduct Amounts vs. Catalyst Age

| Days | % Butyl-benzene | % Non-aromatics | % Diethyl-benzene | % Triethyl-benzene |
|---|---|---|---|---|
| 80  | 0 |  0 | 36 | 13 |
| 100 | 0 | −2 | 11 |  0 |
| 120 | 0 | −2 | 13 |  1 |
| 140 | 0 | −1 | 26 |  4 |
| 160 | 0 | −1 | 27 |  5 |
| 180 | 0 | −1 | 28 |  5 |

*Percents based on EB = 100%

It is to be understood that while illustrative embodiments have been depicted and described, modifications thereof can be made by one skilled in the art without departing from the spirit and scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Also, it is within the scope of this disclosure that the embodiments disclosed herein are usable and combinable with every other embodiment disclosed herein, and consequently, this disclosure is enabling for any and all combinations of the embodiments disclosed herein. Other and further embodiments, versions and examples of the invention may be devised without departing from the basic scope thereof and the scope thereof is determined by the claims that follow.

What is claimed is:

1. A method of forming ethylbenzene comprising:
   introducing a benzene input stream that contains at least 95 wt. % benzene to an alkylation reaction zone having a plurality of catalyst beds containing an alkylation catalyst, wherein the alkylation catalyst comprises a cerium promoted beta zeolite;
   introducing a hydrocarbon gas to each catalyst bed in the alkylation reaction zone, thereby contacting the benzene with the hydrocarbon gas in the presence of the alkylation catalyst under alkylation conditions to produce a product stream containing ethylbenzene and to deactivate the alkylation catalyst, wherein the hydrocarbon gas is in a benzene:hydrocarbon gas weight ratio of 28:1 or less per catalyst bed;
   recovering the product stream from the alkylation reaction zone, wherein the product comprises 0.8 wt. % or less of butylbenzene; and
   regenerating the deactivated alkylation catalyst to produce a regenerated alkylation catalyst by:
      taking a reactor of the alkylation reaction zone offline;
      purging the alkylation catalyst with an inert gas at a purging temperature;
      heating the alkylation catalyst to a first temperature for a time period sufficient to provide an output stream having an oxygen content of about 0.5%;
      heating the alkylation catalyst to a second temperature higher than the first temperature for a time period sufficient to provide an output stream having an oxygen content of about 2.0%, wherein the first temperature and the second temperature are from about 50° C. to about 200° C. above the purging temperature; and
   reusing the regenerated alkylation catalyst.

2. The method of claim 1, wherein the hydrocarbon gas is present in a benzene:hydrocarbon gas weight ratio ranging from 2:1 to 28:1 per catalyst bed.

3. A method of forming ethylbenzene comprising:
   contacting benzene with a hydrocarbon gas in a plurality of catalyst beds;
   wherein the hydrocarbon gas is present in a benzene:hydrocarbon gas weight ratio of 28:1 or less per catalyst bed;
   wherein the contact occurs in the presence of an alkylation catalyst comprising a cerium promoted beta zeolite disposed within the plurality of catalyst beds of an alkylation reaction zone under conditions sufficient to deactivate the alkylation catalyst and to produce a product stream comprising ethylbenzene and 0.8 wt. % or less of butylbenzene;
   recovering the product stream from the alkylation reaction zone; and
   regenerating the deactivated alkylation catalyst to produce a regenerated alkylation catalyst by:
      taking a reactor of the alkylation reaction zone offline;
      purging the alkylation catalyst with an inert gas at a purging temperature;
      heating the alkylation catalyst to a first temperature for a time period sufficient to provide an output stream having an oxygen content of about 0.5%;
      heating the alkylation catalyst to a second temperature higher than the first temperature for a time period sufficient to provide an output stream having an oxygen content of about 2.0%, wherein the first temperature and the second temperature are from about 50° C. to about 200° C. above the purging temperature; and
   reusing the regenerated alkylation catalyst.

* * * * *